United States Patent [19]

Kovacevic et al.

[11] Patent Number: 5,032,510

[45] Date of Patent: Jul. 16, 1991

[54] METHOD FOR EXPRESSION AND SECRETION IN BACILLUS

[75] Inventors: Steven Kovacevic; James R. Miller, Indianapolis, both of Ind.

[73] Assignee: Eli Lilly and Company, Indianapolis, Ind.

[21] Appl. No.: 210,151

[22] Filed: Jun. 17, 1988

Related U.S. Application Data

[63] Continuation of Ser. No. 96,768, Sep. 11, 1987, which is a continuation of Ser. No. 654,435, Sep. 26, 1984, abandoned.

[51] Int. Cl.$^5$ .................. C12P 21/00; C12P 21/02; C12N 15/74; C12N 1/21
[52] U.S. Cl. ................. 435/69.1; 435/252.31; 435/320.1; 435/69.4; 435/69.5; 435/69.2; 435/69.3; 435/69.51; 435/69.52; 435/69.6; 435/69.7; 435/69.8; 435/69.9
[58] Field of Search ............... 435/68, 70, 71, 91, 435/172.1, 172.3, 252.3, 252.31, 252.35, 320; 536/27; 935/14, 29, 39, 41, 44, 47, 48, 72, 74

[56] References Cited

U.S. PATENT DOCUMENTS 4,783,405  11/1988  Kovacevic et al. .................. 435/68

FOREIGN PATENT DOCUMENTS 0036259  9/1981  European Pat. Off. ......... 435/172.3
0057976  6/1982  European Pat. Off. ......... 435/172.3

OTHER PUBLICATIONS

Lovett et al., "Bacillus subtilis as a Host for Molecular Cloning", Methods in Enzymology 68: 342 (1979).
*Webster's New Collegiate Dictionary*, G. & C. Merriam Company, (1979), Springfield, Mass., p. 461.
Shortle, 1983, Gene 22:181.
Palva, 1982, Gene 19:81.
Palva et al., 1982 Proceedings National Academy of Science, U.S.A. 79:5582.
Derwent Abstract 37323 E/19 (1982).
Saunders et al., 1984, J. Bacteriology 157:718.
Fairweather et al., 1983, Infectious Immunology 41:1112.
U.S. patent application Ser. No. 459,792.
Palva et al., 1983, Gene 22:229.

*Primary Examiner*—James Martinell
*Attorney, Agent, or Firm*—Joseph A. Jones; Leroy Whitaker

[57] ABSTRACT

The present invention discloses a novel method for expressing and secreting a functional polypeptide in Bacillus including the vectors and transformants for the practice thereof. The vectors comprise the transcriptional and translational activity sequence, and optionally the signal peptide coding sequence, of the *Staphylococcus aureus* nuclease gene. The vectors and transformants are useful for the production and secretion of human hormones such as human proinsulin.

43 Claims, 3 Drawing Sheets

Figure 1

Restriction Site Map of
Plasmid pOW440
(5.7kb)

Figure 2

Restriction Site Map of
Plasmid pOW448
(9.5kb)

Figure 3

Restriction Site Map of
Plasmid pOW341
(5.3kb)

METHOD FOR EXPRESSION AND SECRETION IN BACILLUS

This application is a continuation of application Ser. No. 07/096,768 filed on Sept. 11, 1987, which is a continuation of application Ser. No. 06/654,435 filed on Sept. 26, 1984.

SUMMARY OF THE INVENTION

The present invention comprises a novel method for expressing and secreting a functional polypeptide in Bacillus including vectors and transformants for the practice thereof. The aforementioned vectors comprise the transcriptional and translational activating sequence and optionally the signal peptide coding sequence of the *Staphylococcus aureus* nuclease gene and also a DNA sequence that codes for a functional polypeptide. The vector components are ligated such that the polypeptide is expressed and optionally secreted upon appropriate transformation.

The present invention provides a method and associated vectors for the expression and secretion of useful polypeptides in Bacillus and other host cells. Heretofore, the development and exploitation of recombinant DNA technology in Bacillus has been retarded and made especially difficult because of the general lack of suitable expression methods and vectors. This paucity of expression methods and vectors is explained in part by the lack of recognition afforded foreign transcription and translation initiation signals in Bacillus. Consequently, the well known trp (Hallewell, R. A. and S. Emtage, 1980, Gene 9:27), lac (Guarante, L. et al., 1980, Cell 20:543 and Roberts, T. M. et al., 1979, Proc. Nat. Acad. Sci. USA 76:5596), lpp (Lee, N. et. al., 1981, J. of Bacteriol. 146:861; Zwiebel, L. J. et al., 1981, J. of Bacteriol. 145:654 and Nakamura, K. and M. Inouye, 1979, Cell 18:1109) and Bacteriophage $AP_L$ (Derom, C. et al., 1982, Gene 17:45; Remaut, E. et al., 1981, Gene 15(1):81 and Bernard, H. et al., 1979, Gene 5:59) transcription and translation-directing promoter systems are not functional in Bacillus. Thus, with the exception of a few drug resistance genes, few foreign and practically no eukaryotic genes have been expressed in Bacillus.

The extremely limited ability of Bacillus to recognize transcription and translation signals presently available necessitates the development of new sequences that direct gene expression. Several early attempts at expression include the cloning and expression in *B. subtilis* of the *B. licheniformis* beta-lactamase gene (disclosed in European Patent Office Publication of European Patent Application No. 81300858.8] No. 0036259) and the *B. stearothermophilus* and *B. amyloliquefaciens* α-amylase genes, (respectively disclosed in European Patent Office Publication [of European Patent Application No. 82300158.1] No. 0057976 and Derwent Abstract [of Belgium Patent Application No. BE 891-659]No. 37323 E/19). Modifications of the *B. subtilis* veg promoter and translation signals (disclosed in U.S. Pat. application Ser. No. 458,792) have also been shown useful for directing the expression of heterologous polypeptides in Bacillus. In addition, Palva et al. (Palva et al., 1983, Gene 22:229 and Palva et al., 1982, Proc. Natl. Acad. Sci. USA 79:5582) have succeeded in expressing and secreting foreign gene products in *B. subtilis* by using transcription, translation and secretion signals from the *B. amylolique-faciens* α-amylase gene. About 20 mg of *E. coli* β-lactamase and 500 μg of human interferon per liter were obtained from the culture supernatants. Mosbach (Mosbach et al., 1983, Nature 302:543) has cloned and obtained expression of rat "proinsulin-like" activity at a low level of about 10 μg per liter. Saunders (Saunders et al., 1984, J. Bacteriol. 157:718) reported that a *Staphylococcus aureus* β-lactamase was expressed as one percent of the total protein in *B. subtilis*. The β-lactamase protein, normally secreted in *S. aureus*, was not secreted but was cell-associated in *B. subtilis*. Also, Fairweather, (Fairweather et al., 1983, Infec. Immun. 41:1112) detected *S. aureus* α-hemolysin in *B. subtilis* supernatants, but this cloned gene has not been sequenced and little is known about the α-hemolysin protein.

Staphylococcal nuclease, one of the most extensively studied enzymes physically and biochemically, is produced and secreted by *Staphylococcus aureus*. This enzyme has recently been cloned and expressed in *E. coli* (Shortle, Gene 22:181), but the expression was disappointingly low and the protein was apparently not processed efficiently. As disclosed herein, the *Staphylococcal* nuclease gene, including the signal peptide and nuclease A and B coding regions, has been cloned into *Bacillus subtilis* and shown to be expressed, secreted and properly processed. Biologically active nuclease has been expressed at relatively high levels and analysis by Western blotting demonstrated that the nuclease is secreted into the culture medium and processed to a lower molecular weight protein (nuclease A) while intracellular (or cell-bound) material was not processed and was present as a higher molecular weight nuclease. The Staphylococcal nuclease gene transcriptional, translational and secretional signals are fully functional in Bacillus and therefore can be used for the expression and secretion of Staphylococcal nuclease or any other commercially important polypeptide. This represents a significant advance in the technical art and helps fill the acute need for expression and secretion methods and vectors for use in Bacillus and other gram positive microorganisms.

Gene cloning and expression of products in *Bacillus subtilis* are highly advantageous since the organism is non-pathogenic, does not produce endotoxins and can secrete gene products into the growth medium. In addition, *B. subtilis* has been extensively studied and is the archetype for genetic studies among gram positive micrcorganisms. The method and expression vectors of the present invention are particularly important because they allow for the commercial exploitation of these important advantages.

For purposes of the present invention, as disclosed and claimed herein, the following terms are as defined below.

Recombinant DNA Expression Vector—any replicating or integrating agent, including but not limited to plasmids, comprising a DNA molecule to which one or more additional DNA segments can be or have been added. Transformation—the introduction of DNA into a recipient host cell.

Transformant—a recipient host cell that has undergone transformation.

Restriction Fragment—any linear DNA generated by the action of one or more restriction enzymes.

Transcriptional Activating Sequence—a DNA sequence that directs the transcription of DNA into messenger RNA (m-RNA).

Translational Activating Sequence—a DNA sequence, including the nucleotide triplet that codes for the translational start codon, that directs the translation of m-RNA into a polypeptide.

Functional Polypeptide—a recoverable bioactive entirely heterologous or homologous polypeptide or precursor, a recoverable bioactive polypeptide comprising a heterologous polypeptide and a portion or whole of a homologous polypeptide, or a recoverable bioinactive fusion polypeptide comprising a heterologous polypeptide and a bioinactivating homologous polypeptide which can be specifically cleaved.

Fused Gene Product—a recoverable heterologous polypeptide which is fused with a portion or whole of a homologous or a different heterologous polypeptide.

DETAILED DESCRIPTION OF THE INVENTION

The present invention is a method for expressing a functional polypeptide in Bacillus, said method comprising a) transforming a Bacillus host cell which is rendered competent for transformation with a recombinant DNA expression vector which is selectable and capable of replication in said host cell, said vector comprising 1) the transcriptional and translational activating sequence of the *Staphylococcus aureus* nuclease gene and 2) a DNA sequence that codes for a functional polypeptide, and b) culturing said cell transformed by said vector under conditions suitable for expression of said polypeptide, subject to the limitation 1) that said sequence that codes for a functional polypeptide and said transcriptional and translational activating sequence are immediately adjacent, in translational reading frame and positioned for expression of said functional polypeptide and 2) that said sequence that codes for a functional polypeptide is exclusive of the nucleotide triplet that codes for the N-terminal amino acid of said functional polypeptide when said amino acid is methionine. The invention further comprises the aforementioned method wherein a) the recombinant DNA expression vector further comprises a signal peptide coding sequence, and b) wherein said transformed cells are cultured under conditions suitable for expression and secretion of said functional polypeptide, subject to the limitation 1) that said signal peptide coding sequence is exclusive of the nucleotide triplet that codes for the N-terminal amino acid of said signal peptide when said amino acid is methionine and that said signal peptide coding sequence is positioned for expression immediately adjacent, downstream and in the translational reading frame of said transcriptional and translational activating sequence, 2) that the nucleotide triplet coding for the C-terminus of the signal peptide encoded by said signal peptide coding sequence is immediately adjacent, upstream and in the translational reading frame of said sequence that codes for a functional polypeptide, and 3) that said sequence that codes for a functional polypeptide is inclusive of the nucleotide triplet that codes for the N-terminal amino acid of said functional polypeptide. The present invention also comprises related recombinant DNA expression vectors and transformants.

Figure 1:
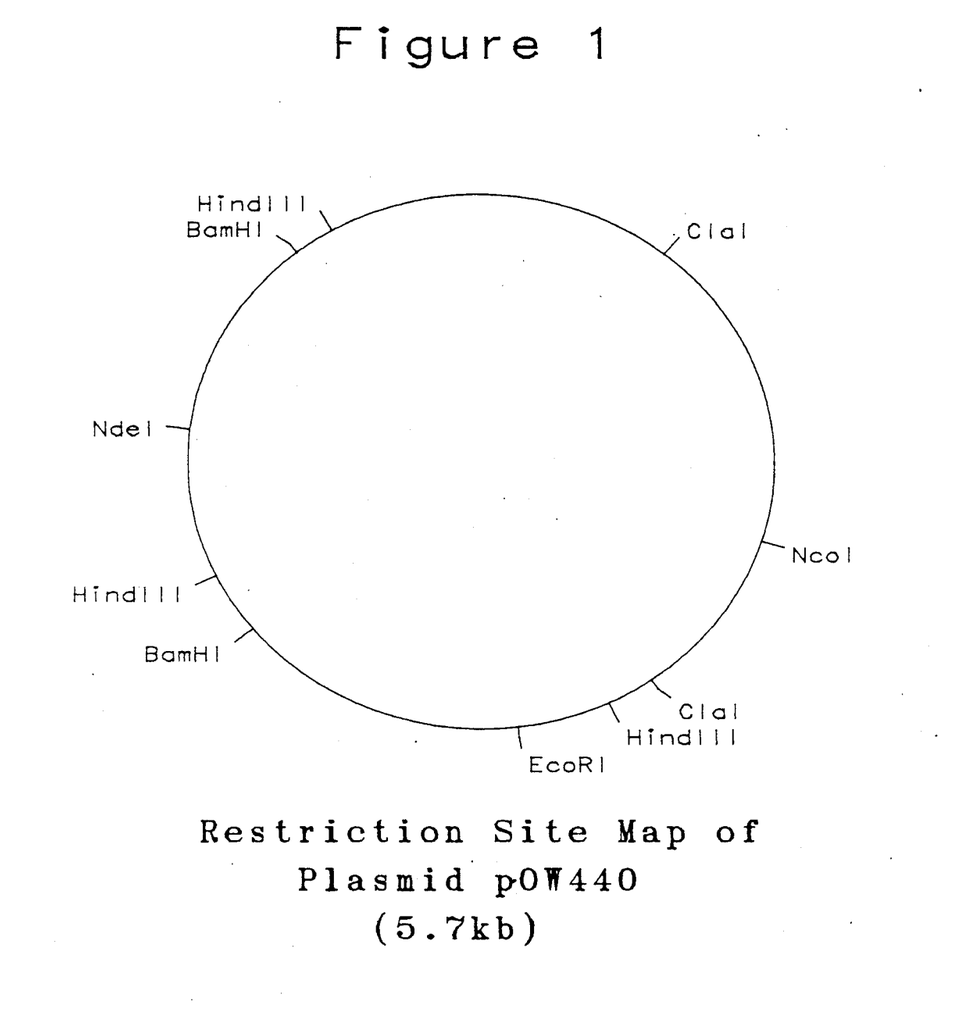
FIG. 1—Restriction Site Map of Plasmid pOW440
FIG. 2—Restriction Site Map of Plasmid pOW448
FIG. 3—Restriction Site Map of Plasmid pOW341
Figure 2:
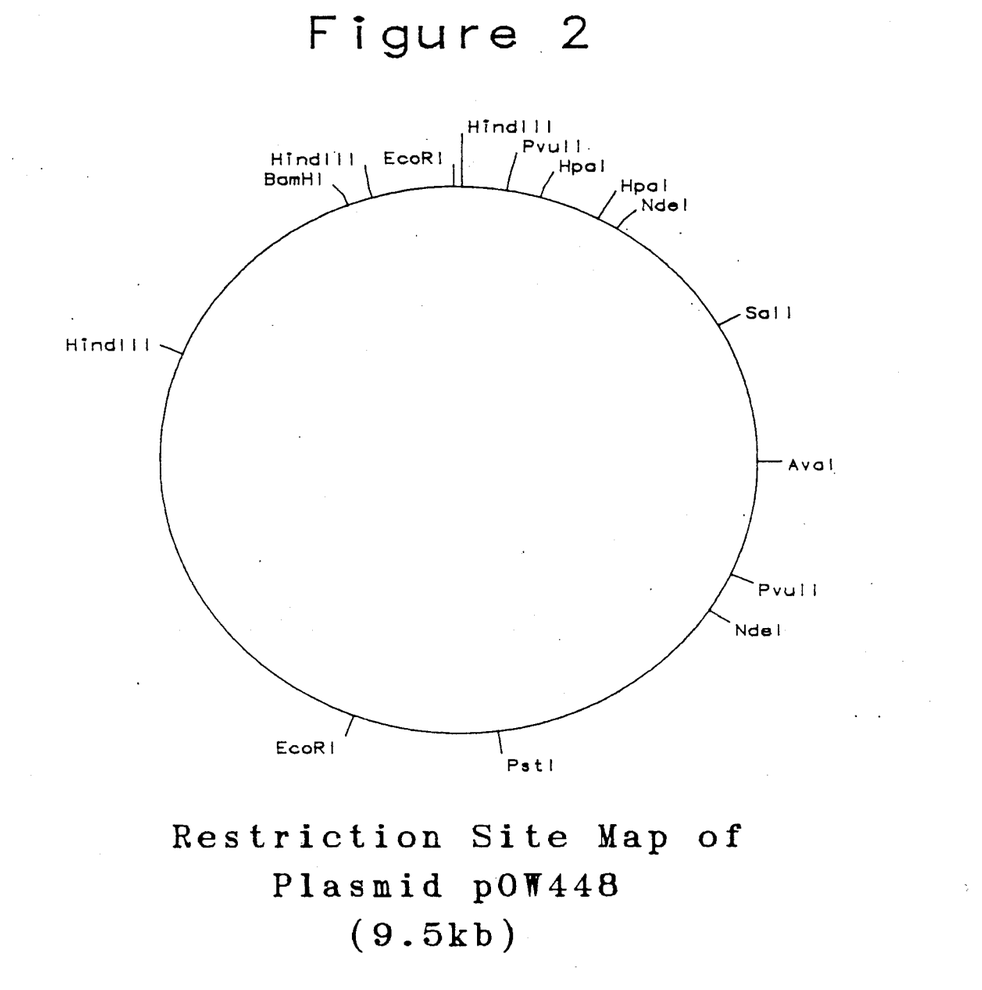
Figure 3:
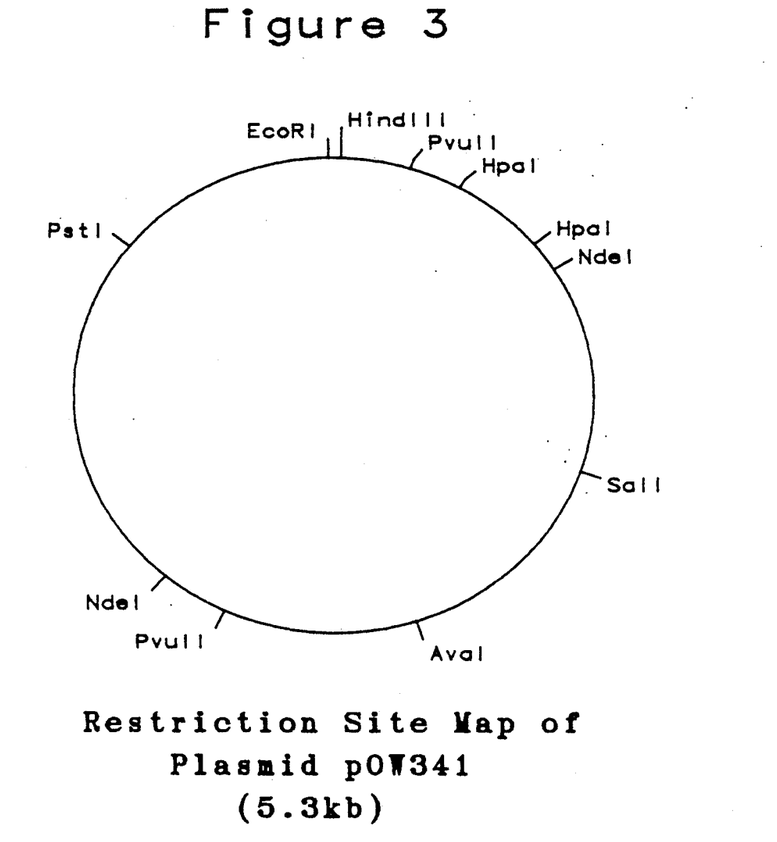

The method of the present invention is best exemplified by constructing recombinant DNA expression vectors that code for the expression and secretion of either Staphylococcal nuclease or other functional polypeptides in Bacillus. The aforementioned nuclease gene was cloned in such a way as to convert the plasmid pFOG301 (Shortle, 1983) Staphylococcal nuclease gene-containing ~1.4 kb HpaII fragment into a BamHI fragment. The actual cloning was done by filling in both the BamHI site of plasmid pBR322 and the isolated HpaII fragment of plasmid pFOG301 by use of Klenow enzyme and then ligating the resultant flush-ended fragments. Because both recombinant DNA and self-ligated vector DNA yield Ap$^r$Tc$^s$ clones, all Ap$^r$ clones were screened for the production of nuclease by a chromogenic plate test. Approximately 15 percent gave a positive indication of nuclease activity. Plasmids from the nuclease positive clones were shown to contain a distinctive BamHI fragment of the same size as the original HpaII fragment. One such plasmid, designated as plasmid pOW50, was BamHI digested and the resultant fragments ligated to similarly digested plasmid pOW430. The resultant plasmid, designated as plasmid pOW440, contains the Staphylococcal nuclease transcriptional, translational, secretional and structural coding sequences. Plasmid pOW440 is functional and codes for the expression and secretion of Staphylococcal nuclease in Bacillus and thus can conveniently be used to exemplify the present method. A restriction site map of plasmid pOW440 is presented in FIG. 1 of the accompanying drawings. The present invention is further exemplified by constructing recombinant DNA expression vectors that code for the expression and secretion of human proinsulin. This was done by ligating the ~295 kb BamHI fragment of plasmid pOW340 into BglII-digested plasmid pOW650. The resulting plasmid, designated as pOW341, was then EcoRI digested and ligated to similarly digested plasmid pOW430 to form the desired plasmid pOW448. Plasmid pOW448 contains the structural gene for human proinsulin covalently linked in translational reading frame with the signal peptide coding and the transcriptional and translational activating sequences of the *Staphylococcus aureus* nuclease gene. Plasmid pOW448 is functional and codes for the expression and secretion of a human proinsulin product in both *E. coli* and Bacillus and thus can conveniently be used to exemplify the present method. A restriction site map of each of plasmids pOW448 and pOW341 is respectively presented in FIGS. 2 and 3 of the accompanying drawings.

The starting materials and certain vectors used to exemplify the present invention are readily available or can be constructed following known procedures. Plasmid pOW440, for example, can be obtained from *Bacillus subtilis* MI112/pOW440, a strain deposited and made part of the permanent stock culture collection of the Northern Regional Research Laboratory, Peoria, Ill. The strain is available as a preferred source and stock reservoir of the plasmid under the accession number NRRL B-15887. The starting material plasmid pOW340 is constructed by ligating 1) the DNA linker sequence wherein
- A is deoxyadenyl,
- G is deoxyguanyl,
- C is deoxycytosyl and
- T is thymidyl;

2) the ~.27 kb HphI-XhoII fragment of plasmid pNM587.4-4, and 3) BamHI-digested plasmid pUC8. Plasmid pNM587.4-4 can be obtained from *E. coli* K12 MM294/pNM587.4-4, a strain deposited and made part of the stock culture collection of the Northern Regional Research Laboratory, Peoria, Ill. It is available as a preferred source and stock reservoir of the plasmid under the accession number NRRL B-15812. Plasmid pUC8 is commercially available from Bethesda Research Laboratories, P.O. Box 6009, Gaithersburg, Maryland. The above linker sequence can be conveniently synthesized by use of known apparatus, such as, for example, the DNA Synthesizer 380A of Applied Biosystems, Foster City, California or can be synthesized in accordance with the procedures of Itakura et al., 1977, Science 198:1056 and Crea et al., 1978, Proc. Nat. Acad. Sci. USA 75:5765.

The plasmid pOW650 starting material is constructed by ligating the ~.65 kb XhoII fragment of plasmid pOW440 into BamHI/BglII-digested plasmid pKC7. Plasmid pKC7 can be obtained from the American Type Culture Collection, Rockville, Maryland and is available without restriction under the accession number ATCC 37084. The plasmid pOW430 starting material is a cloning vector that contains a Bacillus-functional origin of replication and also appropriate selectable markers for use in Bacillus. Plasmid pOW430 can be obtained from *Bacillus subtilis* MII12/pOW430, a strain deposited at the aforementioned Northern Regional Research Laboratory under the accession number NRRL B-15833.

The illustrative plasmid pOW448 codes for the expression and secretion in Bacillus of human proinsulin product. Secretion occurs because the vector coding for proinsulin also codes for the *Staphylococcus aureus* nuclease signal peptide. Signal peptides are short leader regions of amino acids which often comprise newly synthesized polypeptides and which are believed to function in the transport of polypeptides across cell membranes. Signal peptides are typically cleaved from the newly synthesized polypeptides during transport, liberating the desired functional polypeptide in the culture medium. Those skilled in the art will recognize that the present invention is not limited to the use of the aforementioned nuclease signal peptide coding sequence but that various secretory signal peptide sequences include, but are not limited to, the α-amylase signal peptide sequence of *B. amyloliquifaciens* (disclosed in Palva et al., 1981, Gene 15:43 and Palva et al., 1982, Proc. Nat. Acad. Sci. USA 79:5582), the β-lactamase Type I signal peptide sequence of *B. cereus* (disclosed in Sloma and Gross, 1983, Nucleic Acids Res. 11:4997 and Mezes et al., 1983, FEBS Lett. 161:195, the *B. subtilis* levansucrase signal peptide sequence (disclosed in Forret et al., 1984, Biochem. Biophys. Res. Comm. 119:795) and the *B. amyloliquefaciens* subtilisin signal peptide sequence (disclosed in Wells et al., 1983, Nucleic Acids Res. 11:7911). The above secretory coding sequences can be appropriately ligated to the transcriptional and translational activating sequence of the *S. aureus* nuclease gene and also to a sequence that codes for a functional polypeptide. The resultant expression and secretion sequence can be used as a 'cassette' for constructing vectors that further exemplify the present invention.

Skilled artisans will recognize that the transcriptional and translational activating sequence of the Staphylococcus nuclease gene can also be ligated directly to a sequence coding for a functional polypeptide. Such constructions lack a signal peptide coding sequence and thus, upon appropriate transformation, result in intracellular expression of product. Under such conditions the functional polypeptide accumulates within the host cell and is not secreted into the culture medium. Products produced in this way can be isolated by conventional extraction and purification techniques (Methods of Enzymology XXII and XXXIV, Academic Press, New York, N.Y. and EPO Publication Number 0111814, section 5.6) widely used throughout the fermentation industry. In addition, other techniques such as standard chromatography, including cation or anion exchange, sizing resins or bound antibody [affinity], or centrifugation can also be used.

The aforementioned vectors that express but do not secrete functional polypeptides are best constructed by synthetically reconstructing the present transcriptional and translational activating sequence so that the ATG translational start is contained within the recognition sequence for a restriction enzyme at the 3' end. The enzymes NcoI, NdeI, SphI and NsiI (or their isoschizomers) recognize such sequences and are commercially available. Such a synthetically constructed fragment is then inserted into a plasmid vector which contains a unique site for one of these enzymes (e.g. pBR328 and pOW430 both have a unique NcoI site and replicate in *E. coli* and *B. subtilis* respectively) with the upstream (5') end being inserted at another restriction enzyme recognition site (e.g. EcoRI). Ligation and transformation with the recombinant plasmid will regenerate the unique NcoI restriction site. The coding sequence for a functional polypeptide may then be built by a combination of synthetic linkers and purified fragments such that upon ligation and transformation into the bacterial cell, the coding sequence for the functional polypeptide is in the proper orientation and reading frame for expression. More particularly, a sequence coding for human proinsulin may be inserted into a vector by ligating a linker with NcoI and HphI ends, for example, with the unique ~.27 kb HphI-XhoII fragment of plasmid pNM587.4-4 and then combining with an appropriate vector restricted such that it recognizes NcoI and BamHI staggered ends. Those skilled in the art can select any number of plasmid vectors available with the proper sites. Alternatively, one may select a convenient, available restriction site within the signal peptide coding sequence that interrupts the secretion function. Insertion of a proper linker will allow for the ligation of coding sequences for the expression of fused gene products. A NdeI site, located in the Staphylococcal signal sequence about 30 base pairs from the initiation sequence, can be conveniently used for such constructions.

The present invention is particularly versatile and can be applied to the production of any functional polypeptide encoded in a recombinant DNA expression vector. A preferred recombinant DNA expression vector is the plasmid although bacteriophage and other useful vectors will be apparent to those skilled in the art. In addition, various sequences that code for functional polypeptides can be substituted for the illustrative Staphylococcal nuclease and human proinsulin coding sequences specifically exemplified. Such sequences include those that are naturally occurring, non-naturally occurring and those that are in part naturally occurring and in part synthetic or non-naturally occurring. More particularly, illustrative sequences can code for human insulin A-chain, human insulin B-chain, non-human insulin A-chain, non-human insulin B-chain, human proinsulin, human pre-proinsulin human growth hormone, non-human growth hormone, bovine growth hormone, porcine growth hormone, human interferon, non-human interferon, viral antigen, urokinase, human tissue plasminogen activator, interleukin I, interleukin II, growth hormone releasing factor, any hormone, any enzyme or virtually any other polypeptide with research or commercial value.

The recombinant DNA expression vectors and method of the present invention are not limited for use in a single species or strain. To the contrary, the vectors and method are broadly applicable and can be employed using host cells of many taxa, particularly the restrictionless strains of Bacillus, Staphylococcus and *E. coli*. Restrictionless strains are readily selected and isolated from Bacillus and other taxa by conventional procedures and extensions of principles well known in the art (Lomovskaya et al., 1980, Microbiological Reviews 44:206). Host cells of restrictionless strains lack restriction enzymes and therefore do not cut or degrade plasmid DNA upon transformation. For purposes of the present application, host cells containing restriction enzymes that do not cut any of the restriction sites of the present vectors are also considered restrictionless.

Preferred host cells of restrictionless strains of Bacillus, in which the present method and vectors are especially useful, include restrictionless cells of, for example, *B. subtilis*, *B. subtilis* MI112, *B. subtilis* SR22, *B. thuringiensis*, *B. thuringiensis* var. *israeliensis*, *B. cereus*, *B. anthracis*, *B. piliformis*, *B. tropicus*, *B. alvei*, *B. megaterium*, *B. pumilus*, *B. licheniformis*, *B. polymyxa*, *B. macerans*, *B. circulans*, *B. stearothermophilus*, *B. coagulans*, *B. firmus*, *B. brevis*, *B. sphaericus*, *B. pasteurii*, *B. fastidiosus*, *B. larvae*, *B. lentimorbus*, *B. apiarus*, *B. amyloliquifaciens*, *B. laterosporus*, and *B. popillae*.

Preferred host cells of restrictionless strains of Staphylococcus taxa in which the present method and vectors are useful include restrictionless cells of, for example, *S. aureus*, *S. carnosus*, *epidermidis*, and *S. saprophyticus*. The invention is not limited for use in Bacillus and Staphylococcus but can also be used in various *E. coli* host cells. Preferred *E. coli* host cells include, but are not limited to, *E. coli* K12, *E. coli* K12 JA221, *E. coli* K12 HB101, *E. coli* K12 C600, *E. coli* K12 C600$M_k^-R_k^-$, *E. Coli* K12 C600$M_k^-R_k^-$ and *E. coli* K12 RV308.

While all the embodiments of the present invention are useful, some of the present expression vectors are preferred. Accordingly, preferred vectors are plasmids pOW440 and pOW448 and preferred transformants are *Bacillus subtilis* MI112/p440, *B. subtilis* MI112/pOW448, *B. subtilis* SR22/pOW448 and *B. subtilis* SR22/pOW440. Of this preferred group, plasmid pOW448 and transformant B. subtilis SR22/pOW448 are most preferred.

The recombinant DNA expression vectors and transformants of the present invention have broad utility and help fill the need for expression vehicles, especially for use in Bacillus. The present invention thus allows for the genetic expression and secretion in Bacillus of an assortment of important products including those now bioproduced in *E. coli*. This is especially advantageous because large scale fermentation of Bacillus is better known and understood than is fermentation of *E. coli*. In fact, commercial fermentation of *E. coli* is still highly experimental and fraught with difficulty. The present invention circumvents this problem by providing the alternative of producing compounds (some of which are n thesized in *E. coli*) such as, for example, human insulin A-chain, human insulin B-chain human proinsulin growth hormone and the like in Bacillus. This can be done because the present vectors are highly versatile and can accommodate DNA sequences that encode virtually any functional polypeptide. Thus, the present invention allows for flexibility in the choice of hosts and provides a means for using Bacillus in the bioproduction and secretion of polypeptides and other gene products.

The ability of the present transformants to secrete polypeptide products is commercially advantageous. For example, isolation and purification of polypeptides can be done continuously during fermentation without the lytic destruction of host cells. Secretion also affords protection against proteolytic degradation of gene products by naturally occurring protease enzymes. Microorganisms are notorious for producing enzymes which rapidly digest unprotected foreign polypeptides. The present method for secretion circumvents this problem by providing a means for removing susceptible polypeptides from the host cell before proteolytic degradation can occur. In addition, host cells are also protected from the toxic effects of a given gene product since secretion prevents the deleterious effects and possible cell death associated with intracellular build-up.

*Bacillus subtilis*/MI112/pOW430, *B. subtilis* MI112/pOW440 and *E. coli* K12 JA221/pNM587.4-4, as respective sources of plasmids pOW430, pOW440 and pNM587.4-4, can be cultured in a number of ways using any of several different media. Carbohydrate sources which are preferred in a culture medium include, for example, molasses, glucose, dextrin, and glycerol, and nitrogen sources include, for example, soy flour, amino acid mixtures, and peptones. Nutrient inorganic salts are also incorporated and include the customary salts capable of yielding sodium, potassium, ammonium, calcium, phosphate, chloride, sulfate, and like ions. As is necessary for the growth and development of other microorganisms, essential trace elements are also added. Such trace elements are commonly supplied as impurities incidental to the addition of other constituents of the medium.

*Bacillus subtilis* MI112/pOW430 and *B. subtilis* MI112/pOW440 are grown under aerobic culture conditions over a relatively wide pH range of about 5 to 8.5 at temperatures ranging from about 25° to 45° C. For production of plasmids pOW430 and pOW440 in the greatest quantities, however, it is desirable to start with a culture medium at a pH of about 7 and maintain a culture temperature of about 37° C. Culturing *Bacillus subtilis* MI112/pOW430 and *B. subtilis* MI112/pOW440 under the aforementioned conditions results in a reservoir of cells from which the aforementioned plasmids are isolated conveniently by techniques well known in the art.

*E. coli* K12 JA221/pNM587.4-4 is grown under aerobic culture conditions over a relatively wide pH range of about 6.5 to 8 at temperatures ranging from about 25° to 40° C. It is desirable to start with a culture medium at a pH of about 7.2 and maintain a culture temperature of about 37° C. Culturing the *E. coli* cells, under the aforementioned conditions, results in a reservoir of cells from which the plasmids are respectively isolated by techniques well known in the art.

The following examples further illustrate and detail the invention disclosed herein. Both an explanation of and the actual procedures for constructing the invention are described where appropriate.

EXAMPLE 1

Culture of *Bacillus subtilis* MI112/pOW440

A vegetative culture of *Bacillus subtilis* MI112/pOW440 (NRRL B-15887) was conventionally prepared by innoculating sterile Penassay broth (Difco) containing 20 μg/ml of chloramphenicol with the above-specified strain and growing the resultant starter culture at 37° C. with vigorous aeration for about 12 hours. About 2-5% of the volume of the starter culture is then added to fresh sterile Penassay broth and grown at 37° C., until the culture is turbid (about 300-500 Klett units on a Klett Summerson Colorimeter, Klett Mfg. Co., Inc. New York, N.Y., with filter #60). Cell extracts and medium were assayed for nuclease activity in substantial accordance with the procedure of Cuatrecasas et al., 1967, J. Biol. Chem. 242:1541, except that all assays were performed at ambient temperature. Staphylococcal nuclease is produced in high amounts and can be conventionally isolated from the cells and also the culture medium.

EXAMPLE 2

Construction of Plasmid pOW448 and *Bacillus subtilis* MI112/pOW448

A. Construction of Plasmid pOW650 and *E. coli* JA221/pOW650

1. Isolation of Plasmid pOW440

About 10 g (wet wgt) of *Bacillus subtilis* MI112/pOW440 cells (grown in Example 1) were harvested by centrifugation (10 minutes, 4° C, 10,000 rpm), washed in about 50 ml TES (10 mM Tris (pH 8), 10 mM NaCl, 1 mM EDTA) and finally collected again by centrifugation. About 20 ml of TE buffer (containing 25μsucrose) were added followed by 10 mg of lysozyme in 250 μl water. After the mixture was incubated at 37° C. for about 30 minutes, about 100 units of RNase were added. The resultant mixture was again incubated at 37° C. for 30 minutes and, upon being made 1% and 1 M with respect to SDS (sodium dodecyl sulfate) and sodium chloride respectively, the mixture was cooled in an ice bath for about 3 hours. After the lysate was centrifuged (30 minutes, 4° C., 19,000 rpm), the supernatant was adjusted to 31.8 ml with TE and then 28.7 g of cesium chloride and 0.4 ml (10 mg/ml) of ethidium bromide were added. A cesium chloride gradient was established by centrifuging at 49,500 rpm for 16 hours in a VTi50 rotor (Beckman Instruments). The plasmid band was collected and centrifuged at 55,000 rpm in a VTi80 rotor (Beckman Instruments) for 16 hours, then collected again, extracted until all color had disappeared (and then extracted once more) with equal volumes of isoamyl alcohol, dialyzed against dilute TE, ethanol precipitated, and resuspended in 400 μl of TE. The resultant plasmid pOW440 DNA was stored at 4° C. for future use.

2. XhoII Digestion of Plasmid pOW440 and Isolation of the ~.65 kb Fragment

About 20 μl (20 μg) of plasmid pOW440 in water, 1 μl DTT (10 mM Dithiothreitol), 1 μl (10 μg/ml) BSA (bovine serum albumin) 20 μl water, 4 μl (6 units) XhoII restriction enzyme and 5 μl 10X reaction mix* were incubated at 37° C. for about 1 hour. The reaction was terminated by incubation at 65° C. for 10 minutes and then the reaction mixture was cooled on ice, extracted with each of phenol and chloroform:isoamyl alcohol (24:1) and then ethanol precipitated. The desired ~.65 kb restriction fragments were conventionally separated and isolated by agarose gel electrophoresis (Maniatis et al., 1982, Molecular Cloning, Cold Spring Harbor Laboratory, Cold Spring Harbor, N.Y.). The desired ~.65 kb fragments were dissolved in about 10 μl of water.

*Reaction mix for XhoII restriction enzyme was prepared with the following composition. 100 mM Tris-HCl, pH 8 100 mM MgCl₂ .1% Triton X-100

3. BamHI-BglII Digestion of Plasmid pKC7 (ATCC 37084)

The desired digestion was carried out in substantial accordance with the teaching of Example 2A-2 except that BamHI and BglII restriction enzymes, rather than XhoII restriction enzyme, were used. After ethanol precipitation, the digest was dissolved in 10 μl water and used without further purification.

4. Ligation and construction of *E. coli* K12 JA221/pOW650

About 4 μl (3 μg) of the ~.65 kb XhoII fragment of plasmid pOW440, 2 μl (1 μg) of the BamHI-BglII digest of plasmid pKC7, 10 μl water, 2 μl (10 mM) ATP, 1 μl DTT, 2 μl ligation mix* and 1 μl T4 DNA ligase (4 units) were incubated at 16° C. for about 16 hours. The reaction was terminated by incubation at 65° C. for 10 minutes and then, after cooling on ice, the resultant ligated mixture was used to transform *E. coli* K12 JA221 in substantial accordance with the transformation procedure of Lederburg and Cohen, 1974, J. Bacteriology 119:1072, on TY agar (10 g/L tryptone, 5 g/L yeast extract, 5 g/L NaCl, pH 7.2, 15 g/L Agar) containing 80 μg/ml antibiotic ampicillin. The resultant transformants were conventionally cultured and identified and the desired transformants used for the subsequent production and isolation of plasmid pOW650.

*Ligation mix was prepared with the following composition. 500 mM Tris-HCl, pH 7.8 100 mM MgCl₂

B. Construction of Plasmid pOW340 and *E. coli* K12 JA221/pOW340

1. Construction of the DNA Sequence

```
5' GAT CCA ACA GTA TAT AGT GCA ACT TTC GTT AAC CAA CAC TTGT 3'
    ||| ||| ||| ||| ||| ||| ||| ||| ||| ||| ||| ||| |||
3'      GT TGT CAT ATA TCA CGT TGA AAG CAA TTG GTT GTG AAC  5'
``` wherein

A is deoxyadenyl,

G is deoxyguanyl,

C is deoxycytosyl and

The desired fragment was constructed using an automated phosphite triester method. Although any DNA synthesizer can be used, the DNA Synthesizer 380A of Applied Biosystems, Foster City, California is preferred. Those skilled in the art will recognize that the above sequence can also be conventionally synthesized in accordance with the procedure of Itakura et al., 1977, Science 198:1056 and Crea et al., 1978, Proc. Nat. Acad. Sci. USA 75:5765. In addition, an especially preferred synthetic method is disclosed in Hsiung et al., 1983, Nucleic Acid Research 11:3227 and Narang et al., 1980, Methods in Enzymology 68:90. The desired fragment was dissolved in 10 mM Tris, pH 7.8 and stored at −20° C. for future use.

2. HphI-XhoII Digestion of Plasmid pNM587.4-4 and Isolation of the ∼.27 kb Fragment a. Isolation of Plasmid pNM587.4-4

The bacterium *E. coli* K12 JA221/pNM587.4-4 (NRRL B-15812) was cultured in TY broth (the same as TY agar except without the agar) with 100 μg/ml of antibiotic ampicillin according to conventional microbiological procedures. After 18 hours incubation, about 0.5 ml of the culture was transferred to a 1.5 ml Eppendorf tube and centrifuged for about 15 seconds. Unless otherwise indicated, all the manipulations were done at ambient temperature. The resultant supernatant was carefully removed with a fine-tip aspirator and the cell pellet suspended in about 100 μl of freshly prepared lysozyme solution which contained 2 mg/ml lysozyme, 50 mM glucose, 10 mM EDTA (ethylene diaminetetracetate) and 25 mM Tris-HCl (pH 8). After incubation at 0° C. for 30 minutes, about 200 μof alkaline SDS (sodium dodecyl sulfate) solution (0.2 N NaOH, 1% SDS) were added and then the tube was gently vortexed and maintained at 0° C. for 5 minutes. Next, about 150 μl of 3M sodium acetate (prepared by dissolving 3 moles of sodium acetate in a minimum of water, adjusting the pH to 4.8 with glacial acetic acid and then adjusting the volume to 1 L) were added.

The tube was maintained at 0° C. for 60 minutes and then centrifuged for 5 minutes to yield an almost clear supernatant. About 0.4 ml of the supernatant was transferred to a second centrifuge tube to which 1 ml of cold ethanol was added. After the tube was held at −20° C. for 30 minutes, the resultant precipitate was collected by centrifugation and the supernatant removed by aspiration. The DNA pellet was dissolved in 200 μl of 0.1 M sodium acetate/0.05 M Tris-HCl (pH 8) and was reprecipitated by the addition of 2 volumes of cold ethanol. After 10 minutes at −20° C., the precipitate was collected by centrifugation and constituted the desired plasmid pNM587.4-4 DNA.

b. HphI-XhoII Digestion of Plasmid pNM587.4-4 and Isolation of ∼.27 kb Fragment

About 20 μl (20 μg) of plasmid pNM587.4-4 in water 2 μl DTT, 1 μl (1000 μg/ml) BSA, 20 μl water, 4 μl (8 units) of each of HphI and XhoII restriction enzymes and 500 μl 10X reaction mix* were incubated at 37° C. for about 1 hour. The reaction was terminated by incubation at 65° C. for 10 minutes. The reaction was terminated by incubation at 65° C. for 10 minutes and then the resultant mixture was cooled on ice, extracted with each of phenol and chloroform:isoamyl alcohol (24:1) and then ethanol precipitated. The desired ∼.27 kb HphI-XhoII restriction fragments were conventionally separated and isolated by acrylamide gel electrophoresis (Maniatis et al., 1982) and then dissolved in about 30 μl of water.

*Reaction mix for HphI-XhoII restriction enzymes was prepared with the following composition: 100 mM KCl 100 mM Tris-HCl, pH 7.5 100 mM MgCl₂ c. BamHI digestion of plasmid

The desired digestion of plasmid pUC8, commercially available from Bethesda Research Laboratory, Gaithersburg, Md., was carried out in substantial accordance with the teaching of Example 2A-2 except that BamHI restriction enzyme and reaction mix*, rather than XhoII restriction enzyme and reaction mix, were used and except that after ethanol precipitation, the digest was dissolved in 10 μl water and used without further purification.

*Reaction mix for BamHI restriction enzymes was prepared with the following composition: 500 mM NaCl 500 mM Tris-HCl, pH 8 100 mM MgCl₂ d. Ligation and Construction of *E. coli* K12 JA221/pOW340

About 2 μl (0.5 μg) of the DNA sequence of Example 2B-1, 3 μl (0.8 μg) of the ∼.27 kb HphI-XhoII fragment of plasmid pNM587.4-4 and 2 μl (1 μg) of the BamHI digest of pUC8 were ligated and *E. coli* K12 JA221 transformed in substantial accordance with the teaching of Example 2A-4. The resultant transformants were conventionally cultured and identified and the desired transformants used for the subsequent production and isolation of plasmid pOW340.

C. Construction of Plasmid pOW341 and *E. coli* K12 JA221/pOW341

1. BglII Digestion of Plasmid pOW650

The desired digestion of plasmid pOW650 was carried out in substantial accordance with the teaching of Example 2A-2 except that BglII restriction enzyme and reaction mix*, rather than XhoII restriction enzyme and reaction mix, were used and except that after ethanol precipitation, the digest was dissolved in 10 μl water and used without further purification.

*Reaction mix for BglII restriction enzyme was prepared with the following composition. 500 mM NaCl 60 mM Tris-HCl, pH 7.5 60 mM MgCl₂

2. BamHI Digestion of Plasmid pOW340

The desired digestion was carried out in substantial accordance with the teaching of Example 2A-2 except that BamHI restriction enzyme and reaction mix, rather than XhoII restriction enzyme and reaction mix, were used and except that after ethanol precipitation, the digest was dissolved in 10 μl water and used without further purification.

3. Ligation and Construction of *E. coli* K12 JA221/pOW341

About 2 μl (0.8 μg) of the BglII digest of plasmid pOW650 and 2 μl (1 μg) of the BamHI digest of plasmid pOW340 were ligated and *E. coli* K12 JA221 transformed in substantial accordance with the teaching of Example 2A-4. The resultant transformants were conventionally cultured and screened for the desired plasmid pOW341. Plasmids with the correct orientation of fragments were identified by a HpaI digestion followed by electrophoresis in an 8% acrylamide gel and analysis of fragments. A restriction site map of plasmid pOW341 is presented in FIG. 3 of the accompanying drawing. A desired E. coli K12 JA221/pOW341 transformant was conventionally cultured and used for subsequent production and isolation of plasmid pOW341.

D. Construction of Plasmid pOW448 and E. coli K12 JA221/pOW448

1. EcoRI Digestion of Plasmid pOW341

The desired digestion was carried out in substantial accordance with the teaching of Example 2A-2 except that EcoRI restriction enzyme and reaction mix*, rather than XhoII restriction enzyme and reaction mix, were used and except that after ethanol precipitation, the digest was dissolved in 10 μl water and used without further purification.

*Reaction mix for EcoRI restriction enzyme was prepared with the following composition: 500 mM NaCl 500 mM Tris-HCl, pH 8 60 mM MgCl₂

2. EcoRI Digestion of Plasmid pOW430

Plasmid pOW430 was isolated from a vegetative culture of Bacillus subtilis MI112/pOW430 (NRRL B-15833) in substantial accordance with the teaching of Example 1. Plasmid pOW430 was then digested in substantial accordance with the teaching of Example 2A-2 except that EcoRI restriction enzyme and reaction mix, rather than XhoII restriction enzyme and reaction mix, were used and except that after ethanol precipitation, the digest was dissolved in 10 μl water and used without further purification.

3. Ligation and Construction of E. coli K12 JA221/pOW448

About 2 μl (1 μg) of each of the EcoRI digests of plasmids pOW341 and pOW430 were ligated and E. coli K12 JA221 transformed in substantial accordance with the teaching of Example 2A-4. The resultant transformants were conventionally cultured and screened for the desired plasmid pOW448. Transformants containing plasmids with both of the fragments were identified by selecting for ampicillin and chloramphenicol resistance. A desired E. coli K12 JA221/pOW448 transformant was conventionally cultured and used for the subsequent production and isolation of plasmid pOW448. A restriction site map of plasmid pOW448 is presented in FIG. 2 of the accompanying drawings.

E. Construction of Bacillus subtilis MI112/pOW448

Bacillus subtilis MI112 can be obtained by conventionally culturing B. subtilis MI112/pOW430 (NRRL B-15833) in the absence of chloramphenicol. The B. subtilis MI112/pOW430 cells spontaneously lose the pOW430 plasmid under the aforementioned culture conditions thus generating the desired chloramphenicol sensitive B. subtilis MI112 strain. Those skilled in the art will recognize and understand that sensitivity to chloramphenicol can be employed for testing and insuring that only B. subtilis MI112 cells that lack the plasmid are selected and used in the Bacillus transformation procedures herein disclosed.

About 50 ml of sterile PAB (Penassay broth) was inoculated with Bacillus subtilis MI112 and incubated at 37° C. until a cell density of 2×10⁸ cells/ml was reached. The cells were then protoplasted, using sterile technique, by pelleting and then resuspending the cells in about 5 ml of SMMP (equal volumes of each of 4x PAB and a solution comprising 1 M sucrose, 0.04 M maleic acid, and .04 M MgCl₂, pH adjusted to 6.5 with NaOH). Next, about 250 μl of lysozyme (20 mg/ml in SMM [0.5 M sucrose, 0.02 M maleic acid, and, 0.02 M MgCl₂, pH adjusted to 6.5 with NaOH]) were added using filter sterilization. The cells were incubated with gentle shaking at 37° C. for about 2 hours. The resultant protoplasts were pelleted, washed with 5 ml SMMP, and then resuspended in 5 ml SMMP. Following centrifugation (25° C., 12 minutes, 2,600 rpm), about 0.1 ml of protoplasts was transformed by adding about 20 μl of a 1:1 mixture comprising plasmid pOW448 DNA and 2X SMM. About 1.5 ml of PEG solution (40 g PEG 6000 [polyethyleneglycol], 50 ml 2X SMM, and water to 100 ml) were then added followed by about 5 ml of SMMP after about 2 minutes. Next, the protoplasts were pelleted, suspended in 1 ml of SMMP, and incubated at 30° C. with gentle shaking for about 2 hours. Aliquots of the resultant suspension were plated on chloramphenicol-containing DM3 regeneration medium which per liter had the following composition.

| 91 g | D-mannitol in 555 ml deionized water containing 12 g agar |
|---|---|
| 10% | Casamino acids 50 ml |
| 10% | Yeast extract 50 ml |
| 20% | Glucose 25 ml |
| 5% | Dipotassium phosphate 100 ml |
| 1M | MgCl₂ 20 ml |
| 10% | Gelatin |

The D-mannitol, casamino acids and yeast extract were autoclaved together. The gelatin was added immediately after autoclaving and the remaining ingredients were added after the mixture had cooled. The medium had a final antibiotic chloramphenicol concentration of 10 μg/ml.

A chloramphenicol resistant colony was selected as the desired Bacillus subtilis MI112/pOW448 strain. The strain was cultured and the identity further confirmed by conventional restriction enzyme and agarose gel electrophoretic analysis (Maniatis et al., 1982), of the constitutive plasmid. The desired Bacillus subtilis MI112/pOW448 transformants were shown to express human proinsulin and also to secrete the proinsulin product into the culture medium. The presence of human proinsulin both intracellularly and in the medium was conventionally determined by radioimmunoassay.

EXAMPLE 3

Derivation Of Bacillus subtilis SR22 and B. subtilis SR22/pOW448

Bacillus subtilis SR22 can be conventionally derived from B. subtilis SR22/pOW440, a strain deposited and made part of the permanent culture collection of the Northern Regional Research Laboratory, Peoria, Illinois, under the accession number NRRL B-15893, by conventionally culturing the organism in the absence of chloramphenicol. The B. subtilis SR22/pOW440 cells spontaneously lose the pOW440 plasmid under the aforementioned culture condition thus generating the desired chloramphenicol sensitive B. subtilis SR22 strain. Those skilled in the art will recognize and understand that sensitivity to the chloramphenicol can be employed for testing and insuring that only B. subtilis SR22 cells that lack the plasmid are selected and used for generating plasmid pOW448 transformants in accordance with the foregoing teaching.

We claim:

1. A method for expressing a peptide in Bacillus, said method comprising
    a) transforming a Bacillus host cell which is rendered competent for transformation with a recombinant DNA expression vector which is selectable and capable of replication in said host cell, said vector comprising
        1) the transcriptional and translational activating sequence of the *Staphylococcus aureus* nuclease gene and
        2) a cloned DNA sequence that codes for a polypeptide, and
    b) culturing said transformed cell under conditions suitable for expression of said polypeptide, subject to the limitation 1) that said cloned DNA sequence that codes for said polypeptide and said transcriptional and translational activating sequence are immediately adjacent, in translational reading frame and positioned for expression of said polypeptide and 2) that said cloned DNA sequence that codes for said polypeptide is exclusive of the nucleotide triplet that codes for the N-terminal amino acid of said polypeptide when said amino acid is methionine.

2. The method of claim 1 wherein said vector is a plasmid.

3. The method of claim 2 wherein the sequence that codes for a polypeptide is selected from the group consisting of sequences that code for human proinsulin, human insulin A-chain, human insulin B-chain, human pre-proinsulin, human growth hormone, bovine growth hormone, porcine growth hormone, growth hormone releasing factor, interferon, interleukin II, an enzyme, and a hormone.

4. The method of claim 3 in which the sequence that codes for a polypeptide codes for human proinsulin.

5. The method of claim 3 in which the sequence that codes for a polypeptide codes for human pre-proinsulin.

6. The method of claim 3 in which the sequence that codes for a polypeptide codes for human growth hormone.

7. The method of claim 3 in which the sequence that codes for a polypeptide codes for bovine growth hormone.

8. The method of claim 3 in which the sequence that codes for a polypeptide codes for growth hormone releasing factor.

9. The method of claim 3 in which the sequence that codes for a polypeptide codes for an enzyme.

10. The method of claim 3 in which the sequence that codes for a polypeptide codes for a hormone.

11. The method of claim 3 in which the sequence that codes for a polypeptide codes for human insulin B-chain.

12. The method of claim 1 wherein
    a) said recombinant DNA expression vector further comprises a signal peptide coding sequence, and
    b) said transformed cells are cultured under conditions suitable for expression and secretion of said polypeptide,
    subject to the limitation 1) that said signal peptide coding sequence is exclusive of the nucleotide triplet that codes for the N-terminal amino acid of the encoded signal peptide when said amino acid is methionine and that said signal peptide coding sequence is positioned for expression immediately adjacent, downstream and in the translational reading frame of said transcriptional and translational activating sequence 2) that the nucleotide triplet coding for the C-terminus of the signal peptide encoded by said signal peptide coding sequence is immediately adjacent, upstream and in the translational reading frame of said cloned DNA sequence that codes for said polypeptide, and 3) that said cloned DNA sequence that codes for said polypeptide is inclusive of the nucleotide triplet that codes for the N-terminal amino acid of said polypeptide.

13. The method of claim 12 wherein said vector is a plasmid.

14. The method of claim 13 wherein the transscriptional and translational activating sequence, the signal peptide coding sequence and the sequence that codes for a polypeptide comprise the ~1.4 kb BamHI fragment of plasmid pOW440.

15. The method of claim 13 wherein the transscriptional and translational activating sequence and the signal peptide coding sequence comprise the ~.65 kb XhoII fragment of plasmid pOW440.

16. The method of claim 12 wherein the transscriptional and translational activating sequence and signal peptide coding sequence comprise the ~.65 kb XhoII-BglII fragment of plasmid pOW650.

17. The method of claim 12 wherein the sequence that codes for a polypeptide is selected from the group consisting of sequences that code for human insulin, human insulin A-chain, human insulin B-chain, human proinsulin, human growth hormone, bovine growth hormone, porcine growth hormone, interferon, growth hormone releasing factor, interleukin II, an enzyme, and a hormone.

18. The method of claim 17 in which the sequence that codes for a polypeptide codes for human insulin A-chain.

19. The method of claim 17 in which the sequence that codes for a polypeptide codes for human growth hormone.

20. The method of claim 17 in which the sequence that codes for a polypeptide codes for growth hormone releasing factor.

21. The method of claim 17 in which the sequence that codes for a polypeptide codes for bovine growth hormone.

22. The method of claim 17 in which the sequence that codes for a polypeptide codes for human proinsulin.

23. The method of claim 17 in which the sequence that codes for a polypeptide codes for a human hormone.

24. A recombinant DNA expression vector which is selectable and capable of replication in a Bacillus host cell, said vector comprising
    1) the transcriptional and translational activating sequence of the *Staphylococcus aureus nuclease gene and*
    2) a cloned DNA sequence that codes for a polypeptide, subject to the limitation 1) that said cloned DNA sequence that codes for said polypeptide and said transcriptional and translational activating sequence are immediately adjacent, in translational reading frame and positioned for expression of said polypeptide and 2) that said cloned DNA sequence that codes for said polypeptide is exclusive of the nucleotide triplet that codes for the N-terminal amino acid of said polypeptide when said amino acid is methionine.

25. The recombinant DNA expression vector of claim 24 which is a plasmid.

26. The recombinant DNA expression vector of claim 24 wherein the cloned DNA sequence that codes for said polypeptide is selected from the group consisting of sequences that code for human proinsulin, human insulin A-chain, human insulin B-chain, human pre-proinsulin, human growth hormone, bovine growth hormone, procine growth hormone, growth hormone releasing factor, interferon, interleukin II, an enzyme, and a hormone.

27. The recombinant DNA expression vector of claim 26 wherein the sequence that codes for a polypeptide codes for human growth hormone.

28. The recombinant DNA expression vector of claim 26 wherein the sequence that codes for a polypeptide codes for human proinsulin.

29. The recombinant DNA expression vector of claim 26 wherein the sequence that codes for a polypeptide codes for human insulin B-chain.

30. The recombinant DNA expression vector of claim 26 wherein the sequence that codes for a polypeptide codes for bovine growth hormone.

31. The recombinant DNA expression vector of claim 26 wherein the sequence that codes for a polypeptide codes for growth hormone releasing factor.

32. The recombinant DNA expression vector of claim 26 wherein the sequence that codes for a polypeptide codes for an enzyme.

33. The recombinant DNA expression vector of claim 24 which further comprises a signal peptide coding sequence, and subject to the limitation 1) that said signal peptide coding sequence is exclusive of the nucleotide triplet that codes for the N-terminal amino acid of the encoded signal peptide when said amino acid is methionine and that said signal peptide coding sequence is positioned for expression immediately adjacent, downstream and in the translational reading frame of said transcriptional and translational activating sequence, 2) that the nucleotide triplet coding for the C-terminus of the signal peptide encoded by said signal peptide coding sequence is immediately adjacent, upstream and in the translational reading frame of said cloned DNA sequence that codes for said polypeptide, and 3) that said cloned DNA sequence that codes for said polypeptide is inclusive of the nucleotide triplet that codes for the N-terminal amino acid of said polypeptide.

34. The recombinant DNA expression vector of claim 33 which is a plasmid.

35. The recombinant DNA expression vector of claim 34 which is plasmid pOW440.

36. The recombinant DNA expression vector of claim 34 which is plasmid pOW448.

37. A transformed Bacillus host cell which is rendered competent for transformation with a recombinant DNA expression vector which is selectable and capable of replication in said host cell said vector comprising
1) the transcriptional and translational activating sequence of the Staphylococcus aureus nuclease gene and
2) a cloned DNA sequence that codes for a polypeptide, and
3) culturing said transformed cell under conditions suitable for expression of said polypeptide,
subject to the limitation 1) that said cloned DNA sequence that codes for said polypeptide and said transcriptional and translational activating sequence are immediately adjacent, in translational reading frame and positioned for expression of said polypeptide and 2) that said cloned DNA sequence that codes for said polypeptide is exclusive of the nucleotide triplet that codes for the N-terminal amino acid of said polypeptide when said amino acid is methionine.

38. The transformed Bacillus of claim 37 which is *Bacillus subtilis.*

39. The transformed *Bacillus subtilis* of claim 38 which is *Bacillus subtilis* SR22/pOW440.

40. The transformed Bacillus host cell of claim 37 which further comprises a signal peptide coding sequence, and subject to the limitation 1) that said signal peptide coding sequence is exclusive of the nucleotide triplet that codes for the N-terminal amino acid of the encoded signal peptide when said amino acid is methionine and that said signal peptide coding sequence is positioned for expression immediately adjacent, downstream and in the translational reading frame of said transcriptional and translational activating sequence, 2) that the nucleotide triplet coding for the C-terminus of the signal peptide encoded by said signal peptide coding sequence is immediately adjacent, upstream and in the translational reading frame of said cloned DNA sequence that codes for said polypeptide, and 3) that said cloned DNA sequence that codes for said polypeptide is inclusive of the nucleotide triplet that codes for the N-terminal amino acid of said polypeptide.

41. The transformed Bacillus of claim 40 which is *Bacillus subtilis.*

42. The transformed Bacillus of claim 41 which is *Bacillus subtilis* MI112/pOW440.

43. The transformed *Bacillus of claim 41 which is Bacillus subtilis* SR22/pOW448.

* * * * *